US00PP27722P2

(12) United States Plant Patent
Hofmann

(10) Patent No.: US PP27,722 P2
(45) Date of Patent: Feb. 28, 2017

(54) ***VERBENA* PLANT NAMED 'INVEBPUTOW'**

(50) Latin Name: ***Verbena bonariensis*×*Verbena hybrida***
Varietal Denomination: Invebputow

(71) Applicant: Birgit Hofmann, Rudesheim am Rhein (DE)

(72) Inventor: Birgit Hofmann, Rudesheim am Rhein (DE)

(73) Assignee: Innovaplant Zierpflanzen GmbH & Co. KG, Gensingen (DE)

( * ) Notice: Subject to any disclaimer, the term of this patent is extended or adjusted under 35 U.S.C. 154(b) by 0 days.

(21) Appl. No.: 14/756,437

(22) Filed: Sep. 4, 2015

(51) Int. Cl.
*A01H 5/02* (2006.01)

(52) U.S. Cl.
USPC ..... Plt./308

(58) Field of Classification Search
USPC ..... Plt./308
See application file for complete search history.

*Primary Examiner* — Susan McCormick Ewoldt
(74) *Attorney, Agent, or Firm* — C. A. Whealy

(57) ABSTRACT

A new and distinct cultivar of *Verbena* plant named 'Invebputow', characterized by its upright plant habit; vigorous growth habit; freely branching habit; freely flowering habit; and inflorescences of purple violet-colored flowers that are held above and beyond the foliar plane on strong peduncles.

1 Drawing Sheet

Botanical designation: *Verbena bonariensis*×*Verbena hybrida.*

Cultivar denomination: 'INVEBPUTOW'.

BACKGROUND OF THE INVENTION

The present invention relates to a new and distinct cultivar of *Verbena* plant, botanically known as *Verbena bonariensis*×*Verbena hybrida*, and hereinafter referred to by the name 'Invebputow'.

The new *Verbena* plant is a product of a planned breeding program conducted by the Inventor in Heidesheim, Germany. The objective of the breeding program is to create new upright freely-branching *Verbena* plants with thick stems and large sterile flowers.

The new *Verbena* plant originated from a cross-pollination made by the Inventor in August, 2011 in Heidesheim, Germany of an unidentified proprietary seedling selection of *Verbena bonariensis*, not patented, as the female, or seed, parent with a proprietary selection of *Verbena hybrida* identified as code number Vb10-1000-9, not patented, as the male, or pollen, parent. The new *Verbena* plant was discovered and first selected by the Inventor as a single flowering plant within the progeny of the stated cross-pollination in a controlled greenhouse environment in Heidesheim, Germany in May, 2011.

Asexual reproduction of the new *Verbena* plant by terminal cuttings in a controlled environment in Gensingen, Germany since September, 2011 has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Invebputow'. These characteristics in combination distinguish 'Invebputow' as a new and distinct *Verbena* plant:

1. Upright plant habit.
2. Vigorous growth habit.
3. Freely branching habit.
4. Freely flowering habit.
5. Inflorescences of purple violet-colored flowers that are held above and beyond the foliar plane on strong peduncles.

Plants of the new *Verbena* can be compared to plants of the female parent selection. Plants of the new *Verbena* differ primarily from plants of the female parent selection in the following characteristics:

1. Plants of the new *Verbena* are shorter than plants of the female parent selection.
2. Plants of the new *Verbena* have thicker stems than plants of the female parent selection.
3. Plants of the new *Verbena* flower have not been observed to produce seed whereas plants of the female parent selection produce numerous seeds.

Plants of the new *Verbena* can be compared to plants of the male parent selection. Plants of the new *Verbena* differ primarily from plants of the male parent selection in the following characteristics:

1. Plants of the new *Verbena* are more upright than plants of the male parent selection.
2. Plants of the new *Verbena* are more freely branching than plants of the male parent selection.
3. Plants of the new *Verbena* have larger flowers than plants of the male parent selection.

Plants of the new *Verbena* can be compared to plants of the *Verbena bonariensis* 'Little One', disclosed in U.S. Plant Pat. No. 18,124. In side-by-side comparisons conducted in Bonsall, Calif., plants of the new *Verbena* differed primarily from plants of 'Little One' in the following characteristics:

1. Plants of the new *Verbena* were taller than plants of 'Little One'.
2. Plants of the new *Verbena* were more freely branching than plants of 'Little One'.
3. Plants of the new *Verbena* had larger leaves than plants of 'Little One'.
4. Plants of the new *Verbena* had larger flowers than plants of 'Little One'.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the actual colors of the new *Verbena* plant.

The photograph on the right of the sheet comprises a side perspective view of a typical flowering plant of 'Invebputow' grown in a container.

The photograph on the left of the sheet is a close-up view of a typical flowering plant of 'Invebputow'.

DETAILED BOTANICAL DESCRIPTION

The aforementioned photographs and the following observations and measurements describe plants grown during the summer in 10-cm containers in an outdoor nursery in Bonsall, Calif. and under cultural practices typical of commercial potted *Verbena* production. During the production of the plants, day temperatures averaged 29° C., night temperatures averaged 18° C. and light levels ranged from 7,000 to 10,000 foot-candles. Plants were pinched one time and were eight weeks old when the photographs and description were taken. In the following description, color references are made to The Royal Horticultural Society Colour Chart, 2007 Edition, except where general terms of ordinary dictionary significance are used.

Botanical classification: *Verbena bonariensis*×*Verbena hybrida* 'Invebputow'.

Parentage:

*Female, or seed, parent*.—Unidentified proprietary seedling selection of *Verbena bonariensis*, not patented.

*Male, or pollen, parent*.—Proprietary selection of *Verbena hybrida* identified as code number Vb10-1000-9, not patented.

Propagation:

*Type cutting*.—Vegetative tip cuttings.

*Time initiate roots, summer*.—About five to seven days at day temperatures averaging 27° C. and night temperatures averaging 22° C.

*Time to initiate roots, winter*.—About seven to nine days at day and night temperatures averaging 22° C.

*Time to produce a rooted plant, summer*.—About 21 to 23 days at day temperatures averaging 27° C. and night temperatures averaging 18° C.

*Time to produce a rooted plant, winter*.—About 28 to 30 days at day temperatures averaging 18° C. and night temperatures averaging 16° C.

*Root description*.—Medium in thickness, fibrous; white in color.

*Rooting habit*.—Freely branching; medium in density.

Plant description:

*Plant and growth habit*.—Upright plant habit; freely branching habit with about eight primary lateral branches developing per plant; pinching enhances lateral branch development; vigorous growth habit.

*Plant height*.—About 37 cm.

*Plant diameter* (*spread*).—About 26 cm.

Lateral branch description:

*Length*.—About 37 cm.

*Diameter*.—About 3 mm.

*Internode length*.—About 3 cm.

*Strength*.—Strong.

*Aspect*.—Upright.

*Texture*.—Pubescent.

*Color*.—Close to 146A.

Leaf description:

*Arrangement*.—Opposite, simple; sessile.

*Length*.—About 5.4 cm.

*Width*.—About 1 cm.

*Shape*.—Oblong to lanceolate.

*Apex*.—Acute.

*Base*.—Truncate to slightly auriculate; clasping.

*Margin*.—Irregularly crenate, erose.

*Texture, upper surface*.—Pubescent; coarse and stiff hairs; hirsutulous.

*Texture, lower surface*.—Pubescent, minute.

*Venation pattern*.—Pinnate, arcuate.

*Color*.—Developing leaves, upper and lower surfaces: Close to 146A. Fully expanded leaves, upper surface: Close to N137A; venation, close to 147C. Fully expanded leaves, lower surface: Close to 146B; venation, close to 148C.

Flower description:

*Flower arrangement and habit*.—Sessile salverform flowers arranged in compact rounded compound corymbs; flowers face upward or outwardly; freely flowering habit with about 62 flowers developing per primary inflorescence and about 20 flowers per secondary inflorescences.

*Natural flowering season*.—Plants flower continuously from spring through the summer in California; early flowering habit, plants begin flowering about six weeks after planting.

*Flower longevity*.—Flowers last about four to five days on the plant; flowers persistent.

*Fragrance*.—None detected.

*Inflorescence diameter*.—About 3.4 cm.

*Inflorescence height*.—About 1.7 cm.

*Flower diameter*.—About 3 mm.

*Flower depth* (*height*).—About 8 mm.

*Throat diameter*.—Less than 1 mm.

*Tube length*.—About 5 mm.

*Tube diameter*.—Less than 1 mm.

*Flower buds*.—Length: About 8 mm. Diameter: About 1 mm. Shape: Elongated lanceolate. Color: Close to 85A.

*Corolla*.—Arrangement: Single whorl of five fused petals fused towards the base into a narrow tube. Petal lobe length: About 1 mm. Petal lobe width: About 1 mm. Petal lobe shape: Round. Petal lobe apex: Rounded to shallowly emarginate. Petal margin: Entire. Petal texture, upper and lower surfaces: Smooth, glabrous. Petal luster, upper and lower surfaces: Matte. Throat texture: Pubescent, minute. Tube texture: Pubescent, minute. Color: Petal, when opening, upper surface: Close to N82B. Petal, when opening, lower surface: Close to 85C. Petal, fully opened, upper surface: Close to N82C; with development, color becoming closer to 85D. Petal, fully opened, lower surface: Close to 85B; venation, close to 85D. Throat: Close to 85D. Tube: Close to 85C.

*Calyx*.—Arrangement: Single whorl of five fused sepals fused towards the base into a narrow tube. Sepal length: About 2 mm. Sepal width: About 1 mm. Sepal shape: Narrowly lanceolate. Sepal apex: Acute. Sepal margin: Entire. Sepal texture, upper and lower surfaces: Pubescent, minute. Sepal color, upper and lower surfaces: Close to 146B.

*Peduncles*.—Length, terminal peduncles: About 5.4 cm. Length, axillary peduncles: About 2.7 cm. Diameter: About 2 mm. Strength: Strong. Aspect, terminal peduncles: Erect. Aspect, axillary peduncles: About 45° to 55° from vertical. Texture: Pubescent, minute. Color: Close to 146A.

*Reproductive organs*.—Stamens: Quantity per flower: Four. Filament length: Less than 1 mm; mostly adnate to throat. Filament color: Close to NN155D. Anther shape: Rounded. Anther length: Less than 1 mm. Anther color: Close to 1B. Pollen amount: None observed. Pistils: Quantity: One per flower. Pistil length: About 3 mm. Stigma shape: Rounded. Stigma color: Close to 144A. Style length: About 1.5 cm. Style color: Close to 145D. Ovary color: Close to 144C.

*Fruits and seeds*.—Fruit and seed development have not been observed on plants of the new *Verbena*.

Temperature tolerance: Plants of the new *Verbena* have been observed to tolerate temperatures from about 1° C. to about 40° C.

Pathogen & pest resistance: Plants of the new *Verbena* have not been observed to be resistant to pathogens and pests common to *Verbena* plants.

It is claimed:

1. A new and distinct *Verbena* plant named 'Invebputow' as illustrated and described.

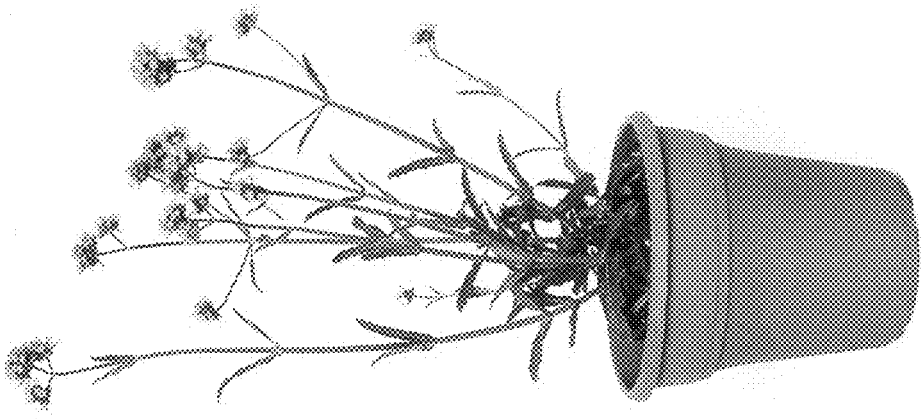
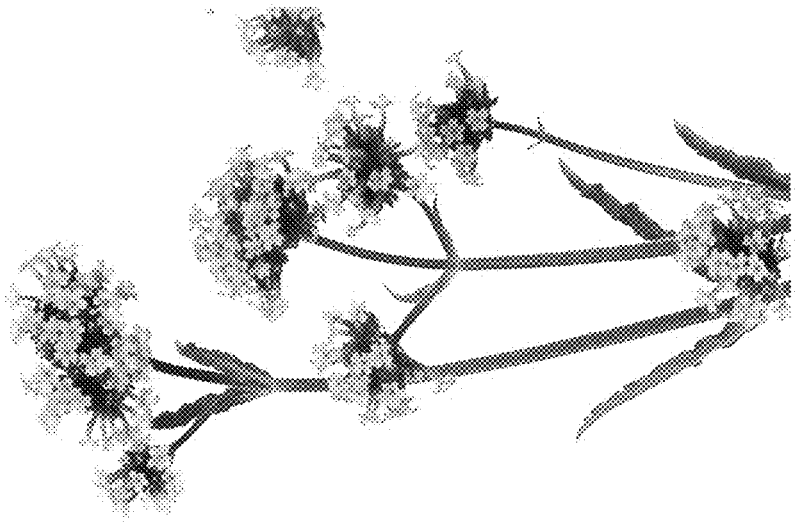

* * * * *